United States Patent
Olives et al.

(10) Patent No.: US 11,355,249 B2
(45) Date of Patent: *Jun. 7, 2022

(54) PET EVALUATION AND TRIAGE SYSTEM

(71) Applicant: Petriage, Inc., Bellevue, WA (US)

(72) Inventors: Casey Stevens Olives, Seattle, WA (US); Shlomo Eliyahu Freiman, Mercer Island, WA (US); Allon Stern Freiman, Seattle, WA (US); Matthew Anthony Fordham, Lake Forest Park, WA (US); Matthew Lee Staroscik, Woodinville, WA (US)

(73) Assignee: Petriage, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/749,231

(22) Filed: Jan. 22, 2020

(65) Prior Publication Data

US 2020/0343001 A1  Oct. 29, 2020

Related U.S. Application Data

(60) Provisional application No. 62/840,260, filed on Apr. 29, 2019.

(51) Int. Cl.
*A61B 5/01* (2006.01)
*G16H 70/20* (2018.01)
(Continued)

(52) U.S. Cl.
CPC ............ *G16H 80/00* (2018.01); *A61B 5/01* (2013.01); *A61B 5/02042* (2013.01);
(Continued)

(58) Field of Classification Search
CPC ........ G16H 80/00; G16H 50/20; G16H 20/00; G16H 70/20; G16H 70/60; G16H 10/60;
(Continued)

(56) References Cited

U.S. PATENT DOCUMENTS

| 6,786,406 B1 * | 9/2004 | Maningas | G06Q 10/10 |
| | | | 235/385 |
| 9,710,757 B2 * | 7/2017 | Gilon | G16H 50/20 |

(Continued)

OTHER PUBLICATIONS

International Search Report and Written Opinion received in International Application No. PCT/US20/30544, dated Jul. 27, 2020, 12 pages.

(Continued)

*Primary Examiner* — Jason S Tiedeman
*Assistant Examiner* — Liza Tony Kanaan
(74) *Attorney, Agent, or Firm* — Perkins Coie LLP

(57) ABSTRACT

A system is provided to provide triage recommendations for animals. The system accesses a syndrome mapping of syndromes to complaints, each syndrome having a triage category. The system accesses a complaint mapping of complaints to symptoms. Each symptom for a complaint has a weight. The system receives indications of a current complaint and current symptoms of an animal. Each current symptom has a score. The system identifies the triage category based on a syndrome to which the current complaint and the current symptoms apply, factoring in the weights and the scores. The system provides a recommendation for the animal based on the identified triage category.

18 Claims, 18 Drawing Sheets

(51) Int. Cl.

| | | |
|---|---|---|
| *G16H 70/60* | (2018.01) | |
| *G16H 50/30* | (2018.01) | |
| *G16H 80/00* | (2018.01) | |
| *G16H 10/60* | (2018.01) | |
| *G16H 40/67* | (2018.01) | |
| *G06N 5/04* | (2006.01) | |
| *A61D 99/00* | (2006.01) | |
| *G16H 40/20* | (2018.01) | |
| *G16H 50/20* | (2018.01) | |
| *G16H 20/00* | (2018.01) | |
| *A61B 5/02* | (2006.01) | |
| *A61B 5/08* | (2006.01) | |
| *A61B 5/11* | (2006.01) | |
| *A61B 5/00* | (2006.01) | |

(52) U.S. Cl.
CPC .......... *A61B 5/0816* (2013.01); *A61B 5/0823* (2013.01); *A61B 5/1118* (2013.01); *A61B 5/41* (2013.01); *A61B 5/4824* (2013.01); *A61D 99/00* (2013.01); *G06N 5/04* (2013.01); *G16H 10/60* (2018.01); *G16H 20/00* (2018.01); *G16H 40/20* (2018.01); *G16H 40/67* (2018.01); *G16H 50/20* (2018.01); *G16H 70/20* (2018.01); *G16H 70/60* (2018.01); *A61B 2503/40* (2013.01); *A61B 2505/07* (2013.01)

(58) Field of Classification Search
CPC ........ G16H 40/67; G16H 40/20; G16H 50/30; A61B 5/02042; A61B 5/0816; A61B 5/0823; A61B 5/1118; A61B 5/41; A61B 5/4824; A61B 5/01; A61B 2505/07; A61B 2503/40; G06N 5/04; G06N 7/005; A61D 99/00; A61D 17/002

See application file for complete search history.

(56) References Cited

U.S. PATENT DOCUMENTS

| | | | |
|---|---|---|---|
| 10,629,304 | B2 | 4/2020 | Leon et al. |
| 2002/0002325 | A1* | 1/2002 | Iliff ........................ G16H 50/20 600/300 |
| 2013/0060576 | A1* | 3/2013 | Hamm ................... G16H 40/67 705/2 |
| 2015/0066520 | A1* | 3/2015 | Leon ...................... G16H 50/70 705/2 |
| 2015/0286784 | A1* | 10/2015 | Hagigi ................... G16H 50/20 705/2 |
| 2017/0262604 | A1* | 9/2017 | Francois ................ G06Q 10/10 |
| 2018/0218126 | A1* | 8/2018 | Salazar .................. G16H 70/20 |
| 2018/0315182 | A1 | 11/2018 | Rapaka et al. |
| 2019/0259499 | A1 | 8/2019 | Hong et al. |

OTHER PUBLICATIONS

Non-Final Office Action received in U.S. Appl. No. 16/752,415 dated Mar. 30, 2020.

Jordan Shefer Peck, Using Prediction to Facilitate Patient Flow in a Health Care Delivery Chain, Feb. 2013, Massachusetts Institute of Technology, pp. 2-84 (Year: 2013).

* cited by examiner

"ate lilies"

Choose all that apply

Ate/exposed to lily
OTHER THAN
true lily or daylily (CHOOSE)
See Synonyms

Ate/exposed to
true lily, daylily,
or unknown lily (REMOVE)

SYNONYMS:
Asiatic hydrid lily, Asiatic lily, Day lily, Daylily, Easter lily, Hemerocallis, Japanese show lily, Lillies, Lilium, Lilium lancifolium, Lilium longiflorum, Lilium philadelphicum, Lilium speciosum, Lilium tigrinum, Lilium Umbellatum, Red lily, True lily, Western lily, Western red lily, Wood lily Hide Synonyms (CONTINUE)

In the meantime, try a different search.

*FIG. 1*

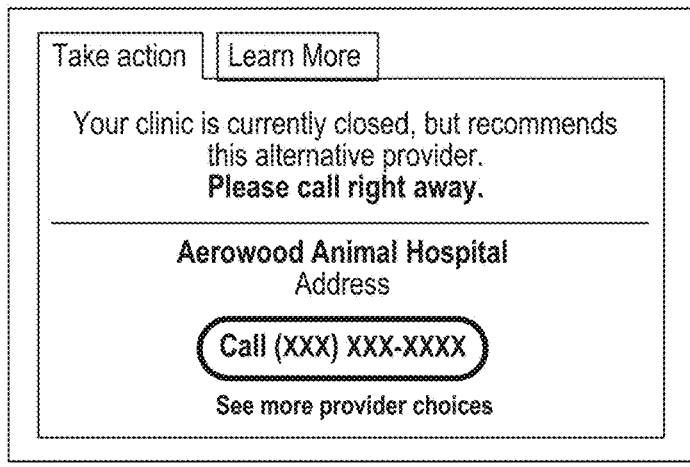
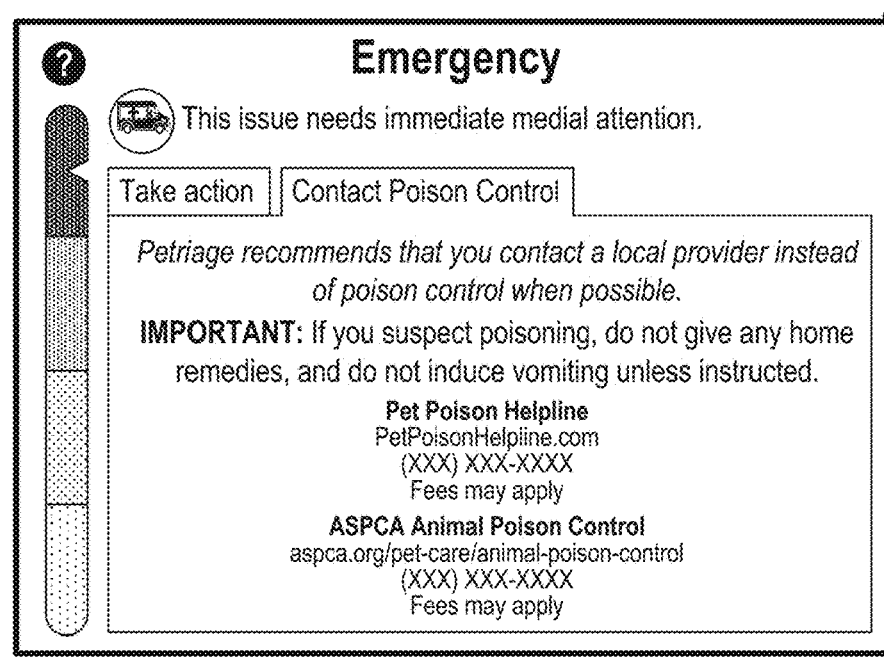
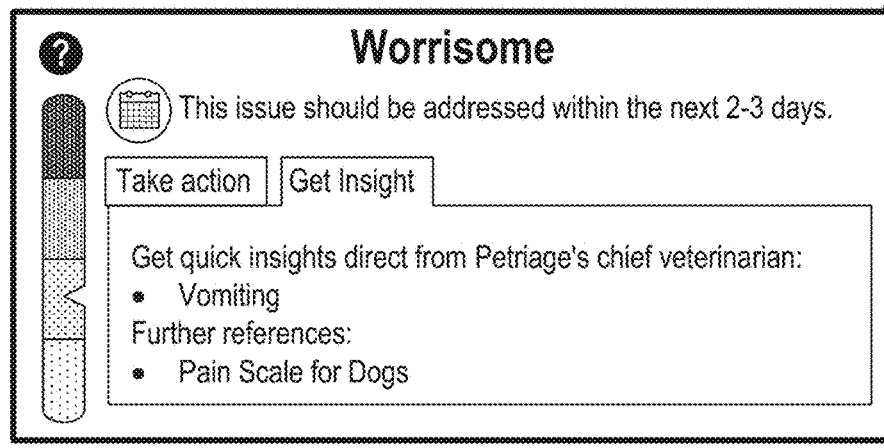
*FIG. 3 (continued)*

400

| Petriage | Dashboard | Petriage Data ▼ | User Data ▼ |

P3TRIAGE / COMPLAINTS / FOXTAIL LODGED IN BODY OR FUR /
Edit Complaint

Complaint Details

410 — Name: Foxtail lodged in body or fur
Common names: Grass seed
Min category: Non-threatening   x ▼
- ☑ Active
- ☑ Male
- ☐ Female
- ☐ Poison
- ☑ Consults allowed Notes: ##GOOD##
Updated name to include "or fur" since this could be quite common.

Symptoms

Complaint Symptom

420 —
Symptom: Are there signs of pus or infected discharge?   x ▼
Weight: 8
- ☑ Active
- ☐ Delete Symptom: Are there signs of inflammation or irritation?   x ▼
Weight: 9
- ☑ Active
- ☐ Delete Symptom: Does your pet have abnormal breathing or effort?   x ▼
Weight: 6
- ☑ Active
- ☐ Delete (Add New Complaint symptom)

(Update Complaint) (Cancel)

| Scale Points | |
|---|---|
| Symptom scale point | |
| Scale point | Label: No Discomfort (Value: 0) |
| Scale point | Label: 2 (Value: 1) |
| Scale point | Label: 3 (Value: 2) |
| Scale point | Label: 4 (Value: 3) |
| Scale point | Label: 5 (Value: 4) |
| Scale point | Label: 6 (Value: 5) |
| Scale point | Label: 7 (Value: 6) |
| Scale point | Label: 8 (Value: 7) |
| Scale point | Label: 9 (Value: 8) |
| Scale point | Label: Extreme Discomfort (Value: 9) |

(Add New Symptom scale point)

Petriage    Dashboard    ( Petriage Data ▼ )    User Data ▼

P3TRIAGE / SYNDROMES / PYOMETRA /
Edit Syndrome

Syndrome Details

| | |
|---|---|
| Name | Pyometra |
| Min category* | Urgent                                    × ▼ |

Pet Details

☐ Male
☑ Female
☑ Intact
☐ Not intact
☐ Size – XS
☐ Size – S
☐ Size – M
☐ Size – L
☐ Size – LX

| | |
|---|---|
| Age rule | Older than                                × ▼ |
| Age in months | 12 |

Previous Diagnoses ( Add Previous Diagnosis )

Pet Species and Breeds

☑ All Cats
☑ All Dogs

Breeds ( Add Breed )

*FIG. 7*

Complaints

Complaint mode: All
"All" will require all entered Chief Complaints be present for a positive match with Syndrome. "Any" will only require one of the Chief Complaints to be present.

First Degree Chief Complaints

Complaint: Vaginal discharge
☐ Delete

Complaint: Lethargic
☐ Delete (Add Chief Complaint)

Second Degree Chief Complaints

Complaint: Feels abnormally warm
☐ Delete

Complaint: Not eating/reduced appetite
☐ Delete (Add Second Degree Complaint)

Follow-Up Symptoms

Symptom mode: All
"All" will require all Follow-Up Symptoms be present for a positive match. "Any" will only require one of the Follow-Up Symptoms to be present.

Symptoms

Symptom: Has your pet been in heat in the last 60 days?
☐ Delete (Add Symptom)

(Update Syndrome) (Cancel)

*FIG. 7 (continued)*

PET EVALUATION AND TRIAGE SYSTEM

CROSS-REFERENCE TO RELATED APPLICATION(S)

This application claims priority to U.S. Provisional Application No. 62/840,260 filed on Apr. 29, 2019, which is hereby incorporated by reference in its entirety.

BACKGROUND

Millions of people own pets. Some pets may need medical attention frequently, and almost all pets need medical attention at some time. To service the medical needs of pets, veterinarians run clinics so that the pet owners can bring their pets to receive medical attention. Most pet owners, however, cannot effectively triage a current condition of a pet to know whether they should seek emergency attention for their pet, call a veterinarian to discuss the pet's condition, wait and see how the condition progresses, and so on. Moreover, the urgency of seeking medical attention for a condition may vary based on the species, breed, age, and so on of the pet. This variation makes it very difficult for the vast majority of pet owners to effectively triage a current condition. As a result, many pets are taken to a clinic even when not warranted by the condition. Conversely, many pets are not taken to a clinic even when warranted by the condition—sometimes with dire consequences.

Because so many pet owners take their pets to a clinic when not warranted by the pet's condition, the overall cost of pet ownership increases. In addition, more clinics and larger clinics are needed to process pets with such conditions. Moreover, a clinic may spend so much time triaging pets with such conditions that the treatment of pets with more serious conditions may be delayed.

BRIEF DESCRIPTION OF THE DRAWINGS

FIG. 1 is a complaint display page that allows an owner to identify a complaint.

FIG. 4 illustrates a specify complaint display page.

FIG. 5 illustrates a specify symptoms display page.

FIG. 6 illustrates specification of a 1-10 scale point option.

FIG. 7 illustrates a specify syndrome display page.

DETAILED DESCRIPTION

Figure 2:
FIG. 2 is a symptom display page that allows entry of symptoms associated with a complaint.

Methods and systems are provided for generating recommendations based on a triage for an animal. In some embodiments, a pet evaluation and triage ("PET") system is a computer-based system that can be used by animal clinics, veterinarians, and other care providers to allow owners of animals (e.g., dogs, cats, and horses), an animal shelter, or other entities responsible for animals to perform a triage on an animal by electronically providing information describing the condition of the animal and receiving recommendations on how to proceed. For example, if the described condition indicates that the condition may be very serious, the recommendation may indicate that the animal may need emergency treatment and have the animal evaluated by a care provider immediately. By providing effective and timely triaging of an animal, the PET system allows a responsible entity to receive an indication of the severity of the condition (e.g., emergency or worrisome) and receive a recommendation on how to proceed. In this way, a responsible entity can seek appropriate attention medical that may avoid the expense and wasted resources (e.g., taking an animal to a care provider) of unnecessary interventions by a care provider.

The PET system also allows care providers to access information relating to the triaging of animals under their care and communicate electronically with the responsible entities to provide advice on care for animals. If the described condition is not very serious but may need attention, the PET system allows a care provider to review the information describing the condition of the animal and to initiate an electronic consultation (e.g., a chat session) to obtain any additional information that is needed and to provide a recommendation to the responsible entity. The recommendation may be to take the animal to a clinic immediately or the next day, call if the condition worsens, and so on. Both the initial triaging by the responsible entity and the electronic consultation contribute to more effective outcomes by identifying the urgency of the pet's condition and proceeding based on that urgency. Because of the technology that supports triaging and electronic consultations, the effectiveness of health care increases while the costs decrease. In the following, the PET system is described primarily in the context of an animal that is a pet, a care provider that is a clinic, and a responsible entity that is a pet owner, although the PET system can be used for any type of animal, care provider, or responsible entity.

In some embodiments, the PET system receives from a pet owner information relating to a pet, a complaint indicating condition of the pet, and ratings of symptoms associated with the complaint. For example, the information relating to the pet may be a signalment that identifies species, breed, sex, age, and so on. A complaint may be that "a foxtail is lodged in the fur of the dog." The symptoms queried may include signs of pus, signs of irritation, abnormal breathing, high temperature, bleeding, and so on. A rating may be based on a scale of 1 to 10, a Boolean value, and so on. For example, a rating of 2 for the symptom of bleeding may indicate that the bleeding appears to be not too serious, while a rating of 10 may indicate that the bleeding is very serious.

After receiving information about the complaint and symptoms, the PET system identifies a triage category for the pet based on weights associated with symptoms associated with the complaint. For example, bleeding may have a higher weight than inflammation because it is likely more urgent to take action when the pet is bleeding than when the pet has inflammation. The triage categories may include emergency, urgent, seek medical advice, non-threatening, and so on. The PET system then provides a recommendation based on the triage category. For example, when the triage category is emergency, the recommendation may be to take the pet to a clinic immediately.

In some embodiments, the PET system may allow an electronic consultation depending on the urgency of the triage category. Each complaint may have an associated base response time indicating by what time the clinic will respond to a request for an electronic consultation. If the base response time is within the consultation hours (e.g., 6:00 a.m. to 9:00 p.m. daily) during which an electronic consultation is available, the PET system sets the response time to the current time plus the base response time. If, however, a portion of the base response time is not within the consultation hours, the PET system sets the response time so that entire base response time is within the consultation hours. For example, if the base response time is four hours, it is 6:00 p.m., and the consultation hours are 6:00 a.m. to 9:00 p.m. daily, the PET system sets the response time to 7:00 a.m. on the next day. Given the worse-case response time, if the pet owner decides to proceed with an electronic consultation, the PET system notifies the clinic of the requested electronic consultation.

FIG. 1 is a complaint display page that allows a pet owner to identify a complaint. The complaint display page 100 includes a search term area 110 and complaint areas 120 and 130. The search term area indicates the search terms that the pet owner specified, namely, "ate lilies." Each complaint area provides information relating to a candidate complaint that matches the search terms. Each complaint area initially contains a "choose" button and a "see synonyms" link. When an owner selects the choose button, the PET system selects the complaint as the indication of the potential problem with the pet and displays a "remove" button to de-select the complaint. When an owner selects the see synonyms link, the PET system displays synonyms relating to the complaint and a hide synonyms link. The owner may select the "try a different search" link to conduct a new search for complaints. When the owner selects the "continue" button, the PET system proceeds to prompt the owner for the symptoms associated with the complaint.

FIG. 2 is a symptom display page that allows entry of symptoms associated with a complaint. The display page 200 includes a complaint area 210, a vitals area 220, and a symptoms area 230. The complaint area confirms the complaint that the pet owner selected on the complaint display page. The vitals area relates to entry of vital information, such as temperature. The symptoms area displays symptoms associated with the complaint, such as discomfort level and energy level. Each symptom has a level bar 231 to allow the pet owner to specify the level of the symptom in a range such as no discomfort to extreme discomfort. Drop-down list 232 allows the owner to choose a time period to indicate when the complaint arose. The symptom relating to vomiting includes yes and no buttons 233.

Figure 3:
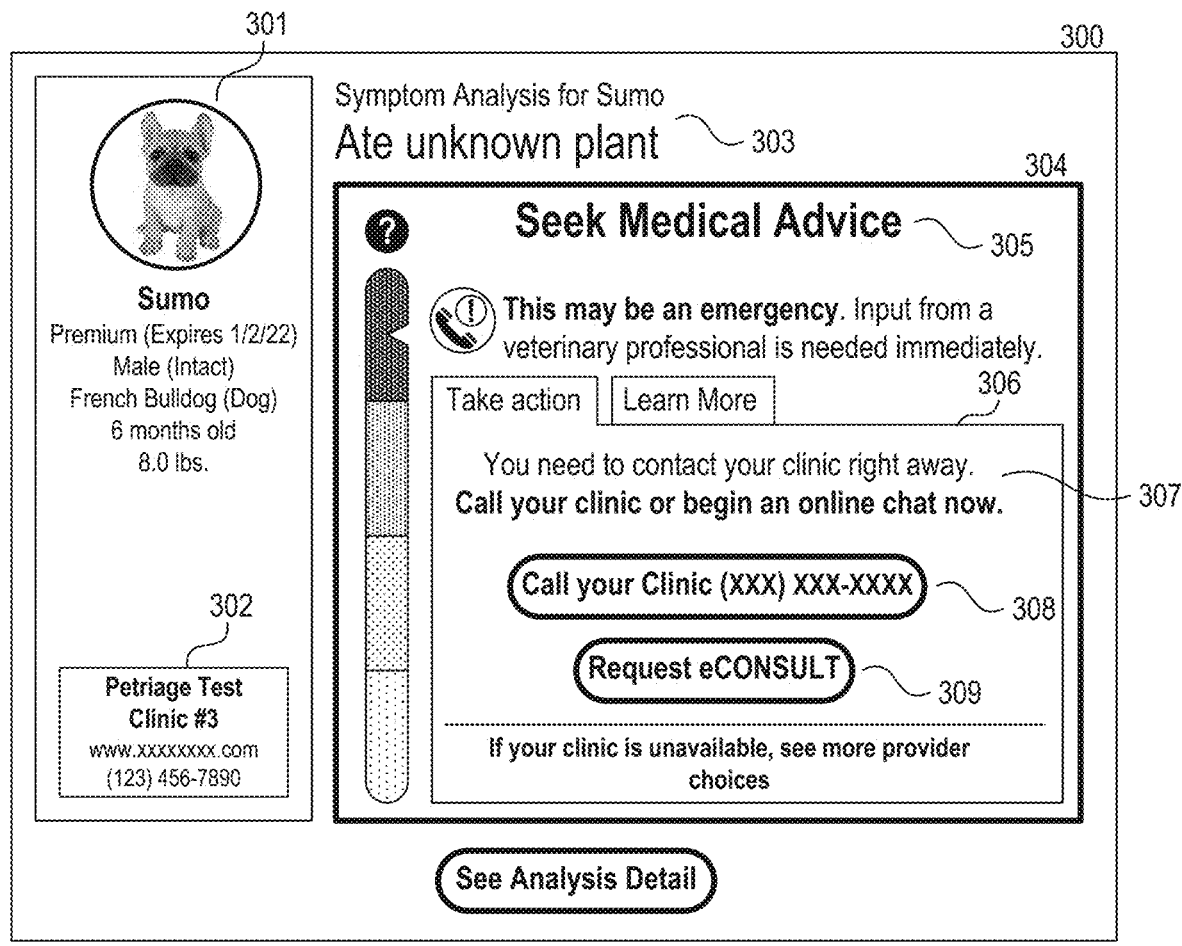
FIG. 3 illustrates a symptom analysis display page.

FIG. 3 illustrates a symptom analysis display page. The symptom analysis display page 300 displays results of the triage analysis based on the complaint and symptoms identified by the pet owner. Area 301 confirms the identity and key information about the patient. Area 302 confirms the identity of the clinic that the pet owner's account is affiliated with. Title area 303 confirms the complaint that the pet owner specified. Recommendation block 304 includes a recommendation title 305 that lists the urgency such as "Emergency," "Urgent," "Seek medical advice," "Worrisome," and "Non-threatening." The recommendation block also summarizes how long the pet owner has to take action. "Take action" tab 306 provides a recommendation 307 (e.g., contact clinic right away), a button 308 to call the clinic, and a button 309 to request an electronic consultation. If the clinic is closed, the take action tab provides information on how to take the action (e.g., wait until clinic opens or go to an after-hours clinic). Emergency Block 320 illustrates a "Contact Poison Control" tab with poison control information that is displayed as appropriate when the complaint is configured to provide the information. Worrisome block 330 illustrates a "Get Insight" tab that is displayed with relevant articles and references as may be configured for each complaint.

The provider of the PET system may allow a clinic to fully specify parameters relating to identification of a triage category so that each clinic can tailor the PET system based on its own expert medical opinions. The parameters include syndromes, complaints, symptoms, weights, and so on. Alternatively, the provider of the PET system may maintain full control over the parameters and not allow a clinic to change the parameters. FIG. 4 illustrates a specify complaint display page. The specify complaint display page 400 allows a complaint and its symptoms to be specified. The display page includes a complaint details area 410 containing a name field and a minimum category field. The minimum category field indicates that if this complaint is specified, the triage category will not be below the minimum category. The checkboxes indicate whether the complaint is currently active, the sex of the animal to which the complaint applies, whether the complaint indicates a poisoning, and whether an electronic consultation is allowed for the complaint (e.g., only for non-emergencies). The complaint symptom area includes each symptom that has been specified for this complaint. Each symptom area 420 includes the name of the symptom, its weight, and whether the symptom is currently active for this complaint. The add symptom button allows a new symptom to be added.

Figure 5:
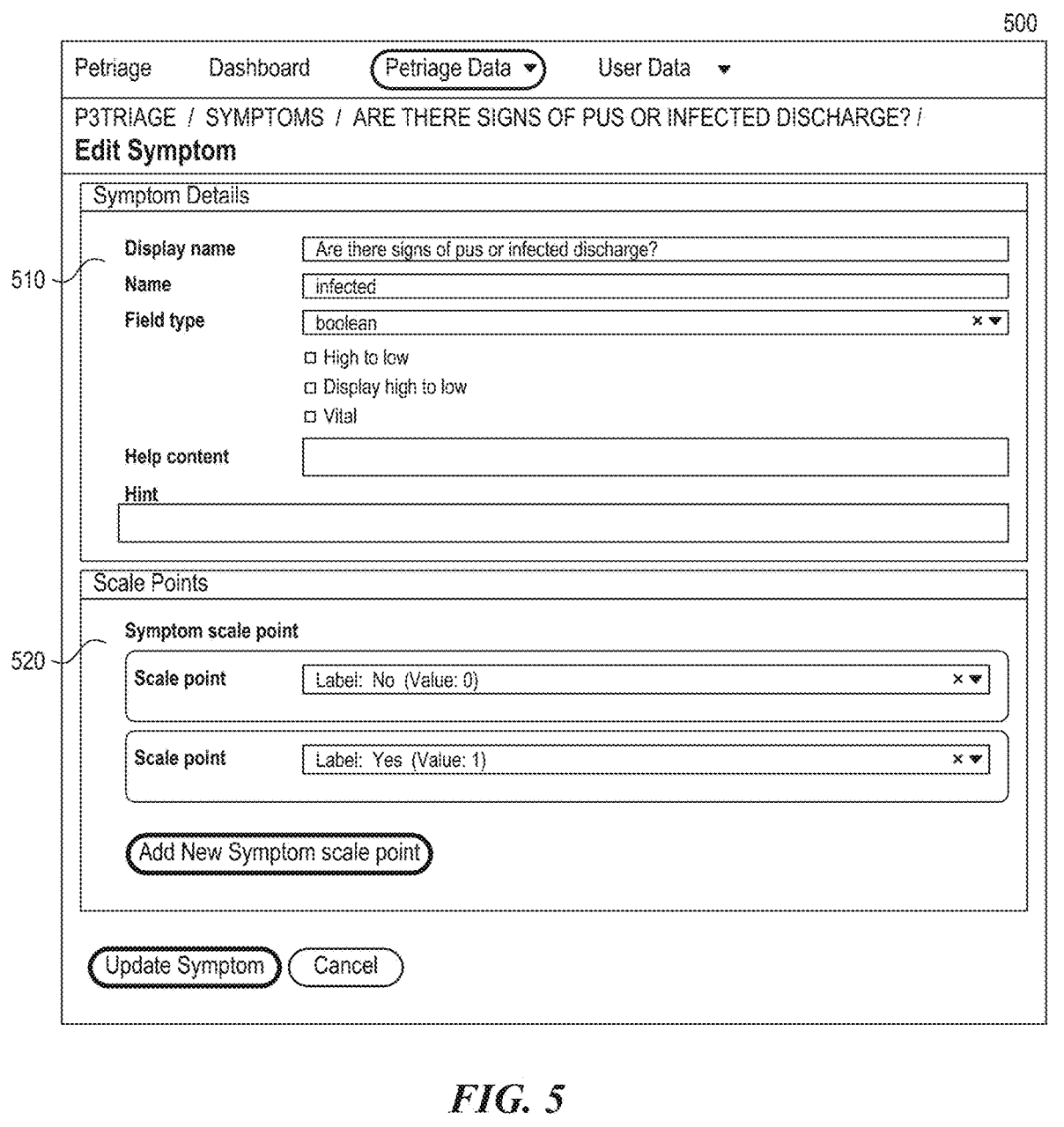

FIG. 5 illustrates a specify symptoms display page. The specify symptoms display page 500 includes a symptom details area 510 and a scale points area 520. The symptom details area includes a display name field and a field type area. The field type area includes a field type field and checkboxes to indicate whether the scoring is high to low, the display is high to low, and the symptom is a vital symptom. The field type specifies the way this symptom is scored. "Boolean" indicates that the answers equate to numerical values of 0 or 1. "Scale" means that the pet owner will see a clickable scale having 10 segments, with the numerical values for the triaging in the range of 0 to 9. "Numeric" means the answer to the question must be in the form of an integer, for example, body temperature. "Select" means that the answers to this question will be selected from a list of predetermined options with each option having a predetermined integer value. The high to low checkbox indicates if the numerical scale value should be inverted before calculation. The display high to low checkbox indicates if the scale displayed to the user should be reversed. The vital checkbox indicates if this symptom is a vital, which means that the symptom will be before other symptoms in the symptom display page. The scale points area specifies the actual numerical answer options offered for the symptom. The drop-down list identifies the scale point options such as Boolean and 1-10. The specify symptoms display page 500 illustrates specification of a Boolean scale point option.

FIG. 6 illustrates specification of a 1-10 scale point option. The symptoms may include the following:
Onset
Severity
Frequency
Energy level
Pain level
Change in condition
Breathing difficulty
Coughing
Mucous membrane coloration
Appetite behavior
Drinking behavior
Urination description
Bowel movements description
Vomiting
Swelling
Signs of infection
Bleeding
Improvement
Discomfort
Temperature (optional)
Respiratory rate (optional)

The PET system solicits rating values for the symptoms from the users in one of the following formats:
Yes/No—For this format, the pet owner is asked a question that solicits a binary response.
Lowest to Highest—For this format, the pet owner is presented with a scale that has clearly demarcated extremes (e.g., "No Discomfort" and "Extreme Discomfort"). The pet owner enters a value on a scale to indicate the relative severity of the symptom with respect to the extremes.
Diverging—For this format, the pet owner can select one of a discrete set of options. These options are "centered" at Normal but can diverge from Normal in two directions. As an example, the PET symptom may ask the pet owner to rate the color of the pet's mucous membranes. In this case, a neutral response is "Normal Pink." However, the pet may also present with "Bright Red" colored gums or "White" colored gums. These represent two different clinical signals, both of which are severe but which diverge from neutral differently.

In order to leverage these symptom responses in the model, each format is transformed as follows:
Yes/No format questions are coded as either 1 or 0, respectively.
Yes=1
No=0
Lowest to Highest questions are coded as an integer from 0 to 9.
No Discomfort=0
Extreme Discomfort=9
Diverging format questions map individual responses to a number. The number in this case captures severity with respect to neutral.
Excessive Drinking=3
More than Normal=2
Slightly More than Normal=1
Normal=0
Slightly Less than Normal=1
Less than Normal=2
Not at All=3

The PET system employs a statistical model with weights (e.g., clinic-specific weights) to codify the relative importance of each symptom to the chief complaint. These weights may take a value between 1 and 10 and are specific to the chief complaint and synonym pair.

At the modeling stage, the PET system may employ the following algorithm to estimate the urgency associated with the chief complaint. The variables for the algorithm are
$Y_i$: The absolute value of the input scale value for symptom i
$n_i$: The absolute maximum value of the input scale value for symptom i
$p_i$: The true underlying probability of observing a value of $Y_i$ out of $n_i$ for symptom i
$w_i$: The weight associated with symptom i
$a, a_i, s, t, \mu$: Scalar model parameters The algorithm employs a Bayesian grouped logistic regression model based on the following assumptions.

$$Y_i | n_i, p_i \sim \text{Binomial}(n_i, p_i)$$

$$\text{logit}(p_i) = a + a_i$$

$$a_i \sim N(0, s^2/w_i^2)$$

$$a \sim N(0, t^2)$$

The hyperparameters s and t are set to reasonable values to ensure non-informative priors on both a and $a_i$. The PET system fits the model using importance sampling. The PET system draws a vector of simulated values of the parameter a from the joint posterior of:

$$(\mu, a_i, s, t) | Y$$

The posterior simulations of a|Y are then transformed to the probability scale using an inverse-logit transform, $\mu$, which represents the urgency of the chief complaint. The simulated values of urgency $\mu$ serve as the basis for the following classification stage.

In order to arrive at a recommendation, the urgency simulations are input into a Bayesian classification framework. The framework outputs one of four categories:
Non-Threatening
Worrisome
Urgent
Emergency The category "Seek medical advice" is generated only by the action of other filters and is not output by the statistical model.

Each of these categories is mapped to a range of urgency represented as R1, R2, R3, and R4. The PET system generates a recommendation as represented by the following equation:

$$\text{Recommendation} = \max_i Pr(\mu \in R_i | \text{Data})$$

The PET system may make personalized recommendations based on historical data of recommendations (1) made by responsible entities, clinics, or individual care providers. For example, once sufficient historical data is collected for a clinic, the PET system may train a machine learning algorithm using animal signalment, complaints, etc. as feature vectors labeled with a clinic's urgency assignment. In this way, the model learns the clinic's preferences for certain levels of urgency.

FIG. 7 illustrates a specify syndrome display page. The display page 700 includes a name and minimum category field. The minimum category field indicates that if this syndrome applies, the triage category will not be below the minimum category. The pet details area specifies the signalment to which this syndrome applies. The add previous diagnosis button is selected to specify a previous diagnosis for this syndrome to apply. The pet species and breeds area specifies the species and breeds to which this syndrome applies. The chief complaints and secondary complaints area allow complaints to be added for this syndrome. A chief complaint indicates a primary condition that signaled to the pet owner that the pet may be experiencing an adverse clinical event. A second degree complaint indicates any ancillary conditions experienced by the pet. The follow-up symptoms area allows questions to be specified to be asked of an owner.

Figure 8:
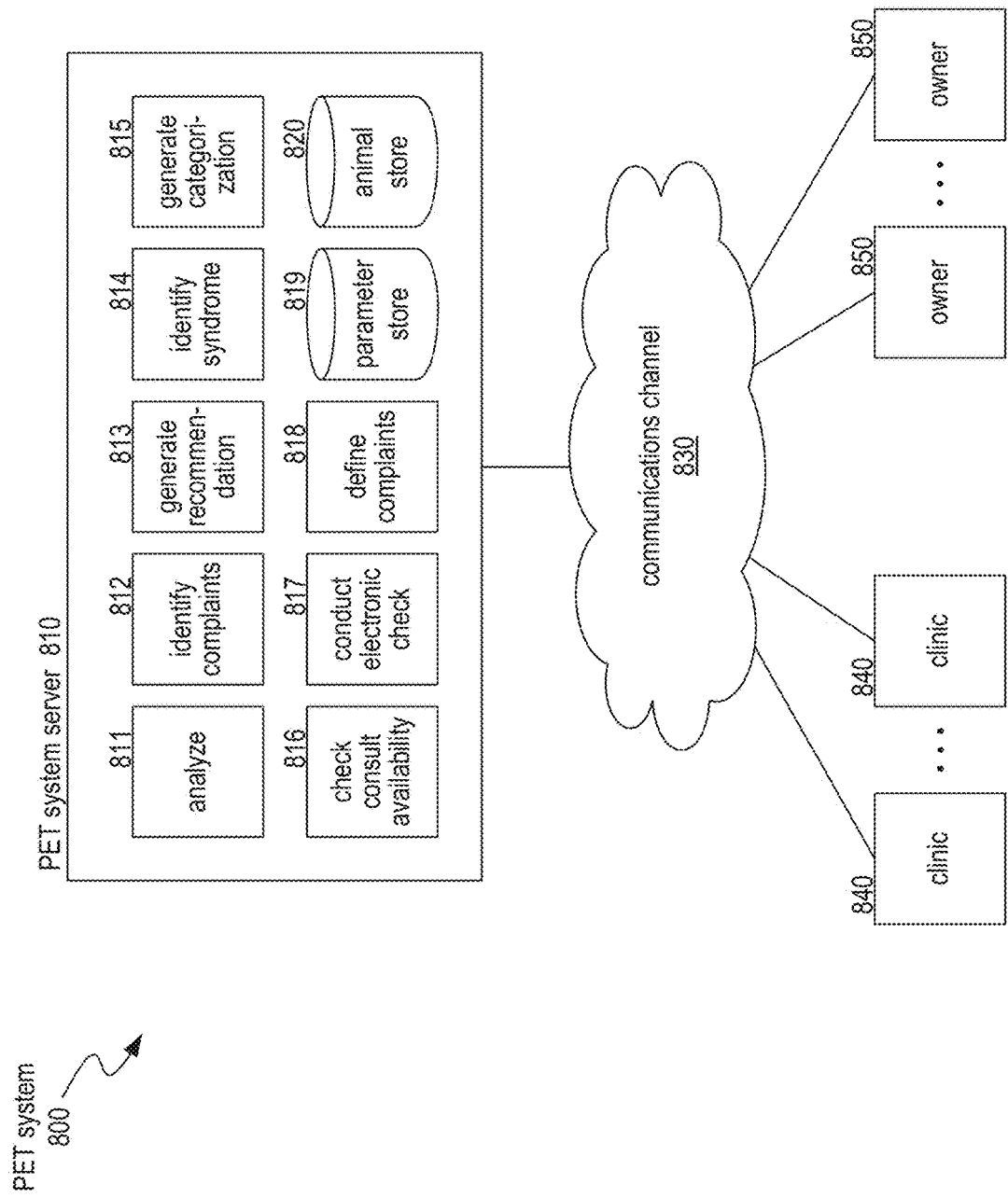
FIG. 8 is a block diagram that illustrates components of the PET system in some embodiments.

FIG. 8 is a block diagram that illustrates components of the PET system in some embodiments. The PET system 800 is implemented on a PET system server 810 and client devices such as clinic computer systems 840 and owner computer systems (e.g., smartphones) 850 via communications channel 830 (e.g., Internet and cellular). The PET system server may also be cloud-based and serve multiple unrelated clinics. The PET system server includes an analyze component 811, an identify complaints component 812, a generate recommendation component 813, an identify syndrome component 814, a generate categorization component 815, a check consultation availability component 816, a conduct electronic check component 817, and a define complaints component 818. The PET system server also includes a parameter store 819 and an animal store 820. The following flow diagrams describe the processing of the components. The client devices may include client-side applications for interfacing with the PET system or a web browser for accessing webpages provided by the PET system. The location of the components and the stores may be distributed so that, for example, a clinic may run the PET system locally and the parameter store and the animal store may be stored locally. The pet owners interact with a client-side app or webpages to identify complaints and symptoms, specify signalment of their animal, and receive recommendations. The animal store contains information on each animal, such as name, species, breed, sex, age, previous diagnoses, and so on. The parameter store stores the parameters defined by the provider of the PET system or a clinic, including symptoms, complaints, and syndromes, as illustrated by the following tables.

| Syndrome |
| --- |
| Name |
| Category (e.g., urgent) |
| Pet Details (e.g., sex, intact, size, age rule, previous diagnoses) |
| Breed |
| Complaints (e.g., 1st and 2nd Degree |
| Chief Complaints, 2nd Degree Complaint) |
| Symptoms (and mode) |

| Complaint |
| --- |
| Name |
| Common Names |
| Minimum Category |

| Complaint |
| --- |
| Sex |
| Poison |
| Consultation Allowed |
| Symptom, weight |

| Symptom |
| --- |
| Name |
| Display Name |
| Field Type (e.g., Boolean) |
| High to Low |
| Display High to Low |
| Vital |
| Scale Points (e.g., No (Value, 0), (Value, 1). Extreme Discomfort (Value, 10)) |

The computing systems (e.g., network nodes or collections of network nodes) on which the PET system may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the classification of the PET system may be performed using a high-performance computing system, while the gathering of symptom information may be performed using a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the PET system. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The PET system may be described in the general context of computer-executable instructions, such as program modules and components, executed by one or more computers, processors, or other devices. Generally, program modules or components include routines, programs, objects, data structures, and so on that perform tasks or implement data types of the PET system. Typically, the functionality of the program modules may be combined or distributed as desired in various examples. Aspects of the PET system may be implemented in hardware using, for example, an application-specific integrated circuit ("ASIC") or field programmable gate array ("FPGA").

Figure 9:
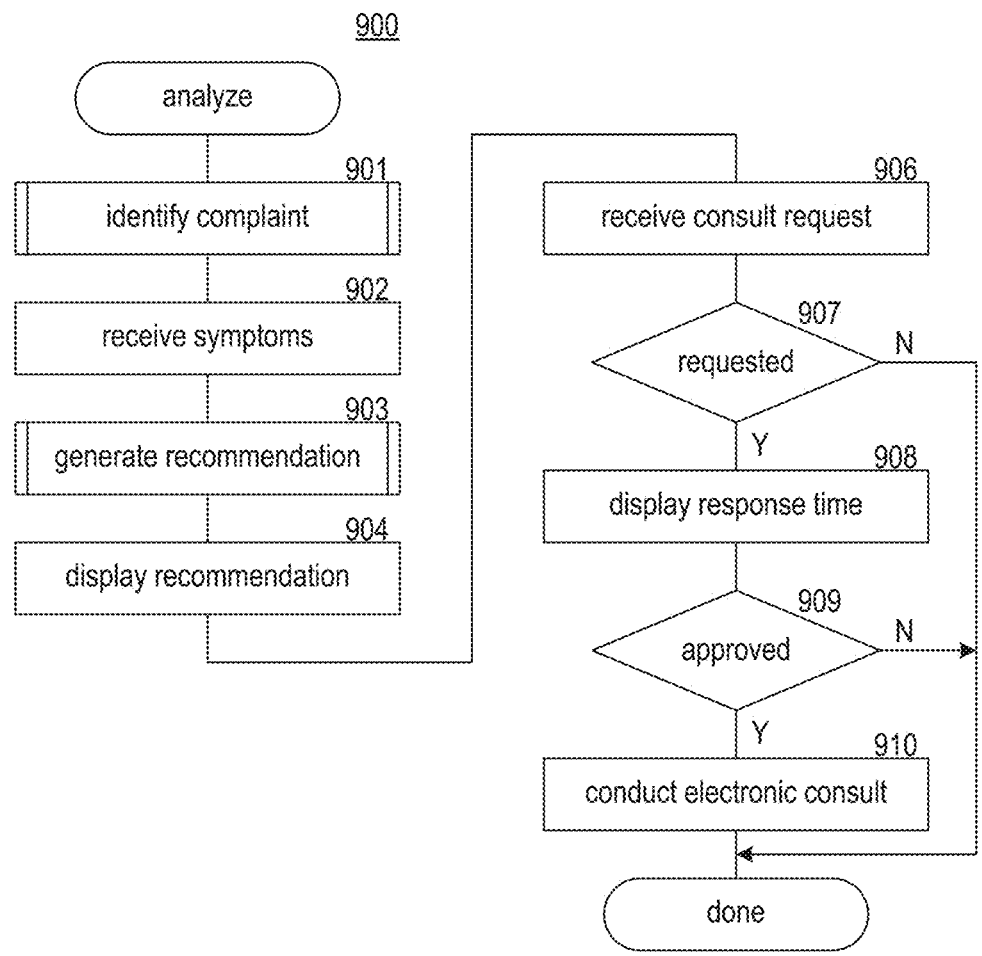
FIG. 9 is a flow diagram that illustrates the processing of an analyze component of the PET system in some embodiments.

FIG. 9 is a flow diagram that illustrates the processing of an analyze component of the PET system in some embodiments. The analyze component 900 generates a recommendation based on complaints and symptoms identified by a pet owner. In block 901, the component invokes an identify complaint component through which the pet owner specifies a complaint relating to the pet. In block 902, the component displays a symptoms display page through which the pet owner can identify the symptoms associated with the complaint that are exhibited by the pet. In block 903, the component invokes a generate recommendation component to generate a triage recommendation. In block 904, the component displays the triage recommendation. In block 906, the component receives a consultation request indicator from the pet owner. In decision block 907, if the consultation is requested, then the component continues at block 908, else the component completes. In block 908, the component calculates and displays a maximum response time for the consultation. In decision block 909, if the pet owner approves the maximum response time, then the component continues at block 910, else the component completes. In block 910, the component directs the conducting of the electronic consultation and then completes.

Figure 10:
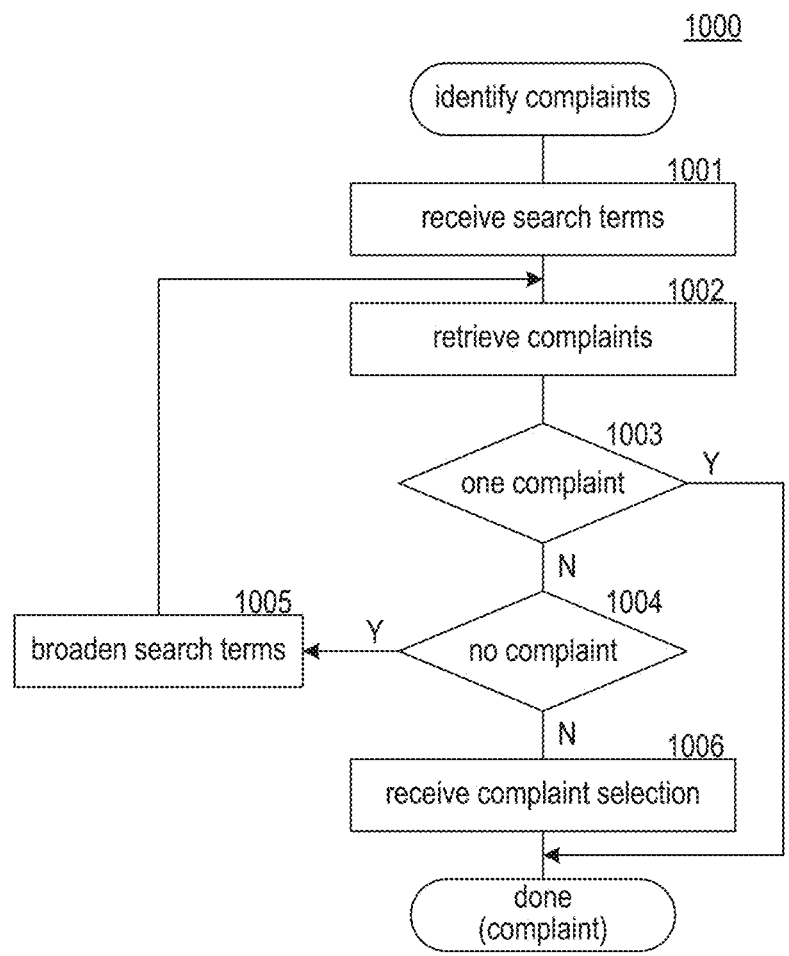
FIG. 10 is a flow diagram that illustrates the processing of an identify complaints component of the PET system in some embodiments.

FIG. 10 is a flow diagram that illustrates the processing of an identify complaints component of the PET system in some embodiments. The identify complaints component 1000 identifies complaints that may match search terms provided by a pet owner. In block 1001, the component receives the search terms from the pet owner. In block 1002, the component retrieves any complaints (i.e., 0, 1, or multiple) that match the search terms and are designated as the chief complaint of a syndrome. In decision block 1003, if one complaint is identified, then the component completes, indicating the complaint, else the component continues at block 1004. In decision block 1004, if no complaint is identified, then the component continues at block 1006, else the component continues at block 1005. In block 1005, the component broadens the search terms and loops to block 1002 to retrieve complaints that match the broadened search terms. In block 1006, the component receives from the pet owner a selection of a complaint and completes, indicating the complaint.

Figure 11:
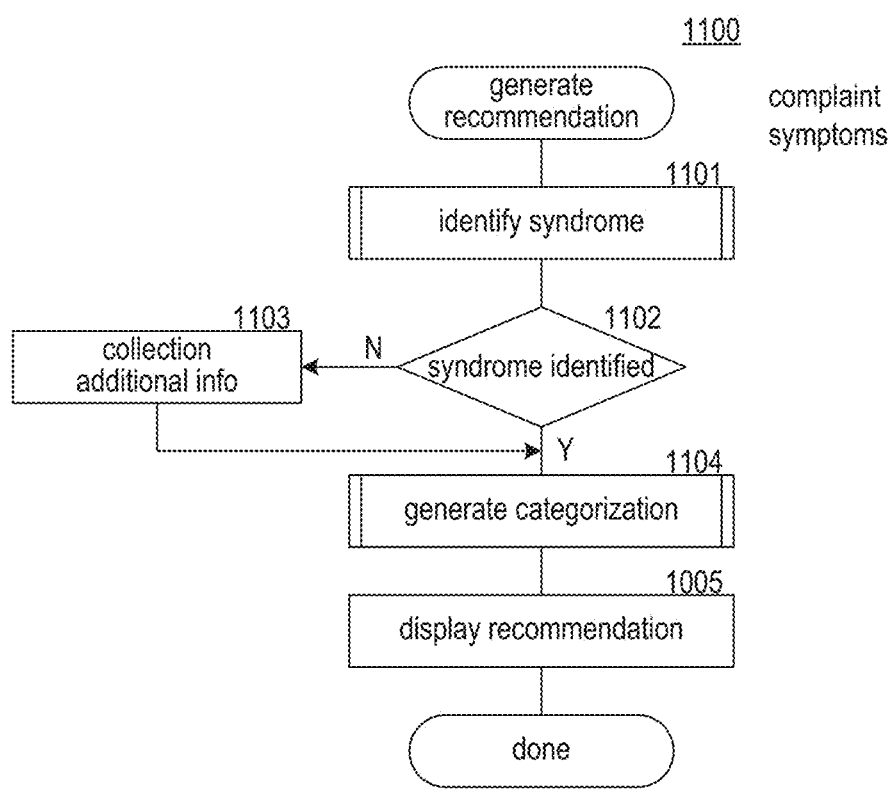
FIG. 11 is a flow diagram that illustrates the processing of a generate recommendation component of the PET system in some embodiments.

FIG. 11 is a flow diagram that illustrates the processing of a generate recommendation component of the PET system in some embodiments. The generate recommendation component 1100 generates a triage recommendation based on a complaint and symptoms identified by a pet owner. In block 1101, the component invokes an identify syndrome component to identify a syndrome associated with the complaint and symptoms. In decision block 1102, if a syndrome is identified, then the component continues at block 1104, else the component continues at block 1103. In block 1103, the component collects additional information from the pet owner. In block 1104, the component invokes a generate categorization component to identify the categorization for the triage recommendation. In block 1105, the component displays the triage recommendation and then completes.

Figure 12:
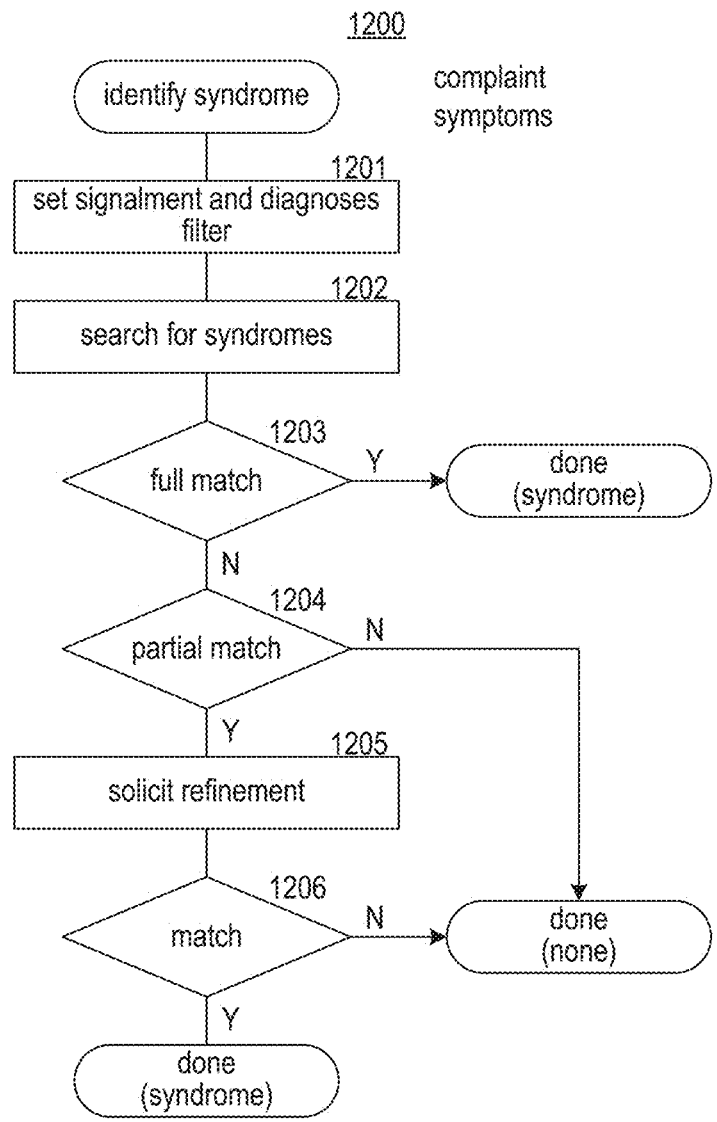
FIG. 12 is a flow diagram that illustrates the processing of an identify syndrome component of the PET system in some embodiments.

FIG. 12 is a flow diagram that illustrates the processing of an identify syndrome component of the PET system in some embodiments. The identify syndrome component 1200 identifies a syndrome based on complaints and symptoms. In block 1201, the component sets a filter based on signalment and diagnosis of the pet. In block 1202, the component searches for syndromes that match the complaints, symptoms, and filter. In decision block 1203, if there is a full match on a chief complaint, then the component completes, indicating the syndrome, else the component continues at block 1204. In decision block 1204, if there is a partial match on the chief complaint or on a second complaint, then the component continues at block 1205, else the component completes, indicating that no syndrome was detected. In block 1205, the component solicits information from the pet owner to refine the partially matching chief complaint. In decision block 1206, if a match is found, then the component completes, indicating the syndrome, else the component completes, indicating that no syndrome was identified.

Figure 13:
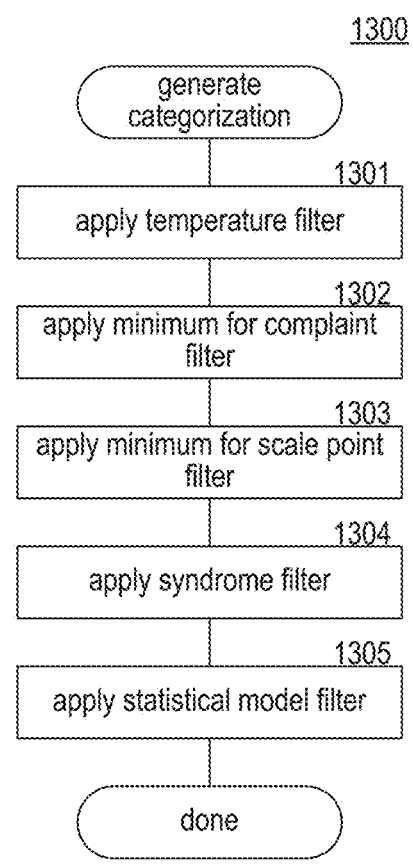
FIG. 13 is a flow diagram that illustrates the processing of a generate categorization component of the PET system in some embodiments.

FIG. 13 is a flow diagram that illustrates the processing of a generate categorization component of the PET system in some embodiments. The generate categorization component 1300 generates a categorization for the triage recommendation. The component applies various filters that generate a categorization and indicates the highest categorization. In block 1301, the component applies the temperature filter to identify a categorization based on the temperature of the pet. In block 1302, the component applies a minimum for complaint filter to identify the minimum categorization allowed for the complaint. In block 1303, the component applies a minimum for scale point filter to identify the minimum categorization based on the scale points of the symptoms. In block 1304, the component applies a syndrome filter to identify the categorization associated with the syndrome. In block 1305, the component applies the statistical model filter to identify a categorization and then completes.

Figure 14:
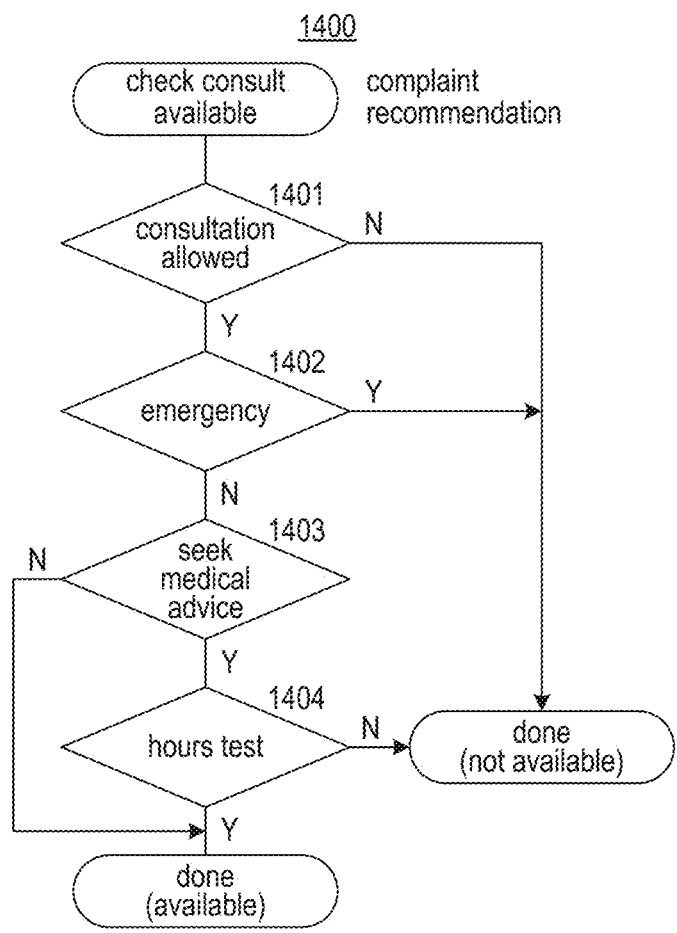
FIG. 14 is a flow diagram that illustrates the processing of a check consultation availability component of the PET system in some embodiments.

FIG. 14 is a flow diagram that illustrates the processing of a check consultation availability component of the PET system in some embodiments. The check consultation availability component 1400 determines whether an electronic consultation is available based on the complaint and recommendation. The availability of a consultation may also be dependent on whether the pet owner signed up for such consultations and whether the initial triage of the pet is still within the base response time. In decision block 1401, if a consultation is allowed for the complaint, then the component continues at block 1402, else the component completes, indicating that a consultation is not available. In decision block 1402, if the recommendation is an emergency, then the component completes, indicating that a consultation is not available. In decision block 1403, if the recommendation is to seek medical advice, then the component continues at block 1404, else the component completes, indicating that a consultation is available. In decision block 1404, if the base response time for the complaint is within the hours of operation of the clinic, then the component completes, indicating that a consultation is available, else the component completes, indicating that a consultation is not available.

Figure 15:
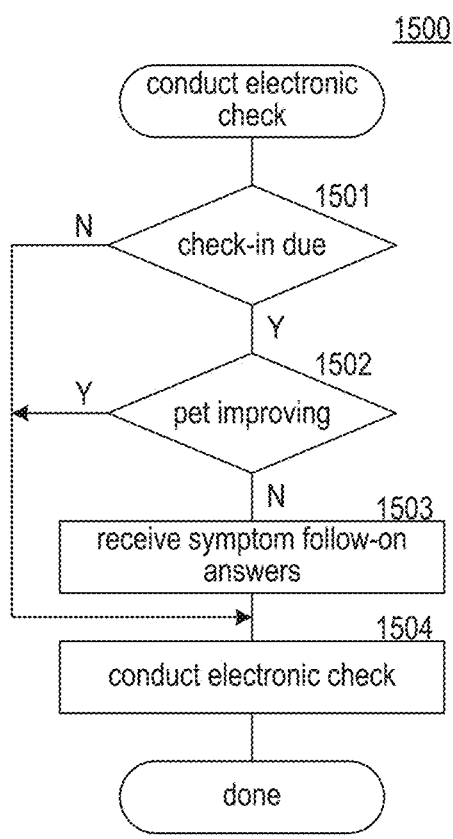
FIG. 15 is a flow diagram that illustrates the processing of a conduct electronic check component of the PET system in some embodiments.

FIG. 15 is a flow diagram that illustrates the processing of a conduct electronic check component of the PET system in some embodiments. The conduct electronic check component 1500 allows a pet owner to update the current condition of their pet. The PET system may send a reminder to a pet owner when an electronic check is due. The PET system may require a pet owner to update the condition of their pet as a precondition for further communications with a clinic. In decision block 1501, if a check-in is due, then the component continues at block 1502, else the component continues at block 1504. In decision block 1502, if the pet owner indicates that the pet is improving, then the component continues at block 1504, else the component continues at block 1503. In block 1503, the component displays a display page through which the pet owner can provide additional information. In block 1504, the component directs the conducting of the electronic check (e.g., via a chat session) and then completes.

Figure 16:
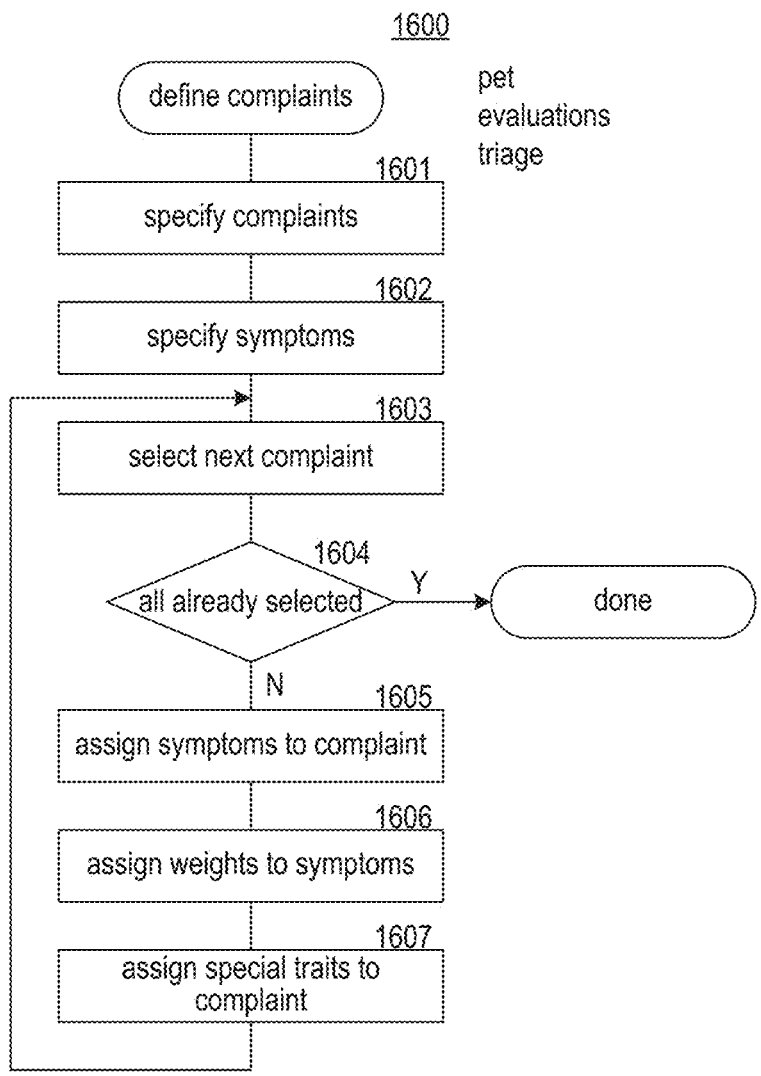
FIG. 16 is a flow diagram that illustrates the processing of a define complaints component of the PET system in some embodiments.

FIG. 16 is a flow diagram that illustrates the processing of a define complaints component of the PET system in some embodiments. The define complaints component 1600 allows a provider of the PET system to specify complaints and symptoms and assign symptoms to complaints. (Alternatively, some clinics may be allowed to define their own complaints and symptoms or to customize the complaints and symptoms defined by the provider.) In block 1601, the component provides a display page through which the provider can specify the possible complaints. In block 1602, the component displays a display page through which the provider can specify possible symptoms of complaints. In block 1603, the component selects the next complaint. In decision block 1604, if all the current complaints have already been selected, then the component completes, else the component continues at block 1605. In block 1605, the component displays a display page through which the provider can assign symptoms to the selected complaint. In block 1606, the component displays a display page through which the provider can assign weights to the symptoms assigned to the selected complaint. In block 1607, the component displays a display page through which the provider can assign any special traits to the selected complaint. The component then loops to block 1603 to select the next complaint.

The following paragraphs describe various embodiments of aspects of the PET system. An implementation of the PET system may employ any combination of the embodiments. The processing described below may be performed by a computing system with a processor that executes computer-executable instructions stored on a computer-readable storage medium that implements the message interface system.

In some embodiments, a method performed by one or more computing systems for providing triage recommendations for animals is provided. The method accesses a syndrome mapping of syndromes to complaints. Each syndrome has a triage category. The method accesses a complaint mapping of complaints to symptoms. Each symptom for a complaint has a weight. The method receives indications of a current complaint and current symptoms of an animal, each current symptom having a score. The method identifies the triage category based on a syndrome to which the current complaint is mapped, the current complaint, and the current symptoms and based on the weights and scores. The method indicates a recommendation for the animal based on the identified triage category. In some embodiments, each symptom for a complaint has a weight and the identifying of the triage category is based on a combination of the scores and the weights of the current symptoms. In some embodiments, the identifying of the triage category is based on a current temperature of the animal. In some embodiments, each complaint is associated with a minimum triage category and the identifying of the triage category is based on the minimum triage category for the current complaint. In some embodiments, each symptom is associated with a minimum triage category and the identified triage category is based on the minimum triage category for a current symptom. In some embodiments, a triage category is selected from a group consisting of emergency, urgent, seek medical advice, worrisome, and non-threatening. In some embodiments, each triage category is associated with a time within which care is to be provided. In some embodiments, the method further indicates that an electronic consultation is not available based on the current complaint and based on either the triage category being emergency or the triage category being seek medical advice when a base response time for seeking medical advice cannot be met; further, when an electronic consultation is available, the method sets a response time based on hours of operation of a clinic. In some embodiments, the method further indicates the response time, receives an indication that a consultation is approved, and directs the conducting of the consultation. In some embodiments, the conducting of the electronic consultation proceeds only after review of the indications of the current complaint and current symptoms. In some embodiments, the method further receives a request for an electronic check and, when an electronic check is due, receives an indication of whether the animal is not improving. When the animal is not improving, the method receives an indication of a symptom and conducts the electronic check.

In some embodiments, a method performed by one or more computing systems for specifying a syndrome relating to analysis of a condition of an animal is provided. The method receives specifications of complaints and receives specifications of symptoms. For each complaint, the method receives an indication of one or more symptoms associated with that complaint and generates a mapping of that complaint to those symptoms. For each syndrome, the method receives a minimum triage category for that syndrome, receives a signalment for that syndrome, and receives one or more complaints for that syndrome. The method generates a mapping of that syndrome to the minimum triage category, the signalment, and the complaint. In some embodiments, the complaints include a chief complaint and a secondary complaint. In some embodiments, for each complaint, the method further receives a weight for each symptom associated with that complaint.

In some embodiments, one or more computing systems for providing triage recommendations for animals are provided. The one or more computing systems comprise one or more computer-readable storage mediums for storing a syndrome mapping of syndromes to complaints, where each syndrome has a triage category, and a complaint mapping of complaints to symptoms, where each symptom for a complaint has a weight. The computer-readable storage mediums further store computer-executable instructions for controlling the one or more computing systems to receive indications of a current complaint and current symptoms of an animal, where each current symptom has a score; identify the triage category based on a syndrome to which the current complaint is mapped, the current complaint, and the current symptoms and based on the weights and scores; and indicate a recommendation for the animal based on the identified triage category. The one or more computing systems further comprise one or more processors for executing the computer-executable instructions stored in the one or more computer-readable storage mediums. In some embodiments, each symptom for a complaint has a weight and the identification of the triage category is based on a combination of the scores of the weights of the current symptoms. In some embodiments, each complaint is associated with a minimum triage category and the identifying of the triage category is based on the minimum triage category for the current complaint. In some embodiments, each symptom is associated with a minimum triage category and the identified triage category is based on the minimum triage category for a current symptom. In some embodiments, the instructions further control the one or more computing systems to indicate that an electronic consultation is not available based on the current complaint, based on the triage category being emergency, and based on the triage category being seek medical advice when a base response time for seeking medical advice cannot be met; and when an electronic consultation is available, the instructions further control the one or more computing systems to set a response time based on hours of operation of a clinic. In some embodiments, the instructions further control the one or more computing systems to indicate the response time, receive an indication that a consultation is approved, and direct the conducting of the consultation.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

The invention claimed is:

1. A method, performed by one or more computing systems having one or more processors, for providing triage recommendations for animals, the method comprising:
   accessing, with at least one processor of the one or more computing systems, a syndrome mapping of syndromes to complaints, each syndrome having a triage category;
   accessing, with at least one processor of the one or more computing systems, a complaint mapping of the complaints to symptoms, each symptom corresponding to a complaint having an associated minimum triage category;
   accessing, with at least one processor of the one or more computing systems, historical data corresponding to the complaints and the symptoms;
   training, with at least one processor of the one or more computing systems, a machine learning model with the accessed historical data corresponding to the complaints and the symptoms;
   receiving, with at least one processor of the one or more computing systems, a current complaint and current symptoms of an animal, wherein each current symptom includes a rating that indicates a seriousness of the current symptoms based on a current condition of the animal and the computing system associates the rating for each current symptom with a maximum rating value for each particular symptom rating, and wherein each current symptom includes a weight that indicates an importance of each symptom;
   identifying, with the at least one or more computing systems, a triage category of a syndrome to which the current complaint is mapped using the accessed syndrome mapping, the accessed complaint mapping, the current complaint, the current symptoms, and the ratings, a minimum triage category, and weight associated with at least one of the current symptoms;
   applying, with at least one processor of the one or more computing systems, the trained machine learning model to the received indications of the current complaint and the current symptoms of the animal to estimate an urgency score, wherein the estimated urgency score is based on a joint posterior distribution of hyperparameters given, for each current symptom, the current rating and its associated a maximum rating and a weight; and
   indicating, with at least one processor of the one or more computing systems, a recommendation for the animal based on the identified triage category and the estimated urgency score identified by applying the trained model.

2. The method of claim 1 wherein the identifying of the triage category is based on a current temperature of the animal.

3. The method of claim 1 wherein each complaint is associated with a minimum triage category and the identifying of the triage category is based on the minimum triage category associated with the current complaint.

4. The method of claim 1 wherein the identified triage category is selected from a group consisting of emergency, urgent, seek medical advice, worrisome, and non-threatening.

5. The method of claim 1 wherein each triage category is associated with a time within which care is to be provided.

6. The method of claim 1 further comprising:
   indicating that an electronic consultation is not available based on the current complaint, based on the triage category being emergency, and based on the triage category being seek medical advice when a base response time for seeking medical advice cannot be met; and
   when an electronic consultation is available, setting a response time based on hours of operation of a clinic.

7. The method of claim 6 further comprising:
   indicating the response time;
   receiving an indication that an electronic consultation is approved; and
   directing the conducting of the approved electronic consultation.

8. The method of claim 7 wherein the conducting of the approved electronic consultation proceeds only after review of the indications of the current complaint and current symptoms.

9. The method of claim 1 further comprising:
   receiving a request for an electronic check;
   when the electronic check is due,
      receiving an indication of whether the animal is not improving; and
      when the animal is not improving, receiving an indication of a symptom; and conducting the electronic check.

10. A method performed by one or more computing systems for specifying a syndrome relating to analysis of a current condition of an animal, the method comprising:
    receiving specifications of complaints;
    receiving specifications of symptoms, each symptom having an associated minimum triage category;
    for each complaint,
       receiving an indication of one or more symptoms associated with that complaint; and
       generating a mapping of that complaint to those symptoms;
    for each syndrome,
       receiving a minimum triage category for that syndrome;
       receiving a signalment for that syndrome;
       receiving one or more complaints for that syndrome; and
       generating a mapping of that syndrome to the minimum triage category, the signalment, and the one or more complaints for that syndrome;
    accessing historical data corresponding to the complaints and the symptoms;
    training a machine learning model based on the accessed historical data corresponding to the complaints and the symptoms;
    receiving indications of a current complaint and current symptoms, each current symptom having a rating that indicates a seriousness of the current symptoms based on the current condition of the animal, and the computing system associates the rating for each current symptom with a maximum rating value for each particular symptom rating, and wherein each current symptom includes a weight that indicates an importance of each symptom;

applying the trained machine learning model to the received indications of the current complaint and the current symptoms to estimate an urgency score, wherein the estimated urgency score is based on a joint posterior distribution of hyperparameters given a current rating, a maximum rating, and the weight of each current symptom; and indicating a recommendation based on the estimated urgency score identified by applying the trained model.

11. The method of claim 10 wherein the complaints include a chief complaint and a secondary complaint.

12. The method of claim 10 further comprising, for each complaint, receiving a weight for each symptom associated with that complaint.

13. One or more computing systems for providing triage recommendations for animals, the one or more computing systems comprising:
one or more computer-readable storage mediums for storing:
a syndrome mapping of syndromes to complaints, each syndrome having a triage category;
a complaint mapping of complaints to symptoms, each symptom for a complaint having an associated minimum triage category; and
computer-executable instructions for controlling the one or more computing systems to:
access historical data corresponding to the complaints and the symptoms;
train a machine learning model with the accessed historical data corresponding to the complaints and the symptoms;
receive a current complaint and current symptoms of an animal, each current symptom having a rating that indicates a seriousness of the current symptoms based on a current condition of the animal, and the computing system associates the rating for each current symptom with a maximum rating value for each particular symptom rating, and wherein each current symptom includes a weight that indicates an importance of each symptom;
identify a triage category of a syndrome to which the current complaint is mapped using the syndrome mapping, the complaint mapping, the current complaint, the current symptoms, and the ratings, a minimum triage category, and weight associated with at least one of the current symptoms;
apply the trained machine learning model to the received indications of the current complaint and the current symptoms of the animal to estimate an urgency score, wherein the estimated urgency score is based on a joint posterior distribution of hyperparameters given, for each current symptom, the current rating and its associated maximum rating and weight; and
indicate a recommendation for the animal based on the identified triage category and the estimated urgency score; and
one or more processors for executing the computer-executable instructions stored in the one or more computer-readable storage mediums.

14. The one or more computing systems of claim 13 wherein each complaint is associated with a minimum triage category and the identifying of the triage category is based on the minimum triage category associated with the current complaint.

15. The one or more computing systems of claim 13 wherein the instructions further control the one or more computing systems to:
indicate that an electronic consultation is not available based on the current complaint, based on the triage category being emergency, and based on the triage category being seek medical advice when a base response time for seeking medical advice cannot be met; and
when an electronic consultation is available, set a response time based on hours of operation of a clinic.

16. The one or more computing systems of claim 15 wherein the instructions further control the one or more computing systems to:
indicate the response time;
receive an indication that an electronic consultation is approved; and
direct the conducting of the electronic consultation.

17. A method performed by one or more computing systems for providing triage recommendations for patients, the method comprising:
accessing a syndrome mapping of syndromes to complaints, each syndrome having a triage category;
accessing a complaint mapping of complaints to symptoms, each symptom corresponding to a complaint having an associated minimum triage category;
accessing historical data corresponding to the complaints and the symptoms;
training a machine learning model with the accessed historical data corresponding to the complaints and the symptoms;
receiving a current complaint and current symptoms of a patient, wherein each current symptom includes a rating that indicates a seriousness of the current symptoms based on a current condition of the animal, and the computing system associates the rating for each current symptom with a maximum rating value for each particular symptom rating, and wherein each current symptom includes a weight that indicates an importance of each symptom;
identifying a triage category of a syndrome to which the current complaint is mapped using the accessed syndrome mapping, the accessed complaint mapping, the current complaint, the current symptoms, and the ratings, a minimum triage category, and weight associated with at least one of the current symptoms;
applying the trained machine learning model to the received indications of the current complaint and the current symptoms of the patient to estimate an urgency score, wherein the estimated urgency score is based on a joint posterior distribution of hyperparameters given, for each current symptom, the current rating and its associated maximum rating and weight; and
indicating a recommendation for the patient based on the identified triage category and the estimated urgency score identified by applying the trained machine learning model.

18. The method of claim 17, wherein the rating of a first current symptom of the patient is provided by a user and corresponds to a seriousness of the first current symptom based on a current condition of the patient and indicates a relative severity of the first current symptom with respect to clearly demarcated extremes.

\* \* \* \* \*

UNITED STATES PATENT AND TRADEMARK OFFICE
CERTIFICATE OF CORRECTION

| | |
|---|---|
| PATENT NO. | : 11,355,249 B2 |
| APPLICATION NO. | : 16/749231 |
| DATED | : June 7, 2022 |
| INVENTOR(S) | : Casey Stevens Olives et al. |

It is certified that error appears in the above-identified patent and that said Letters Patent is hereby corrected as shown below:

In the Drawings

On sheet 1 of 18, in FIG. 1, and on the title page, the illustrative figure, reference numeral 130, Line 3, delete "hydrid" and insert -- hybrid --.

On sheet 1 of 18, in FIG. 1, and on the title page, the illustrative figure, reference numeral 130, Line 8, delete "speclosum," and insert -- speciosum, --.

On sheet 4 of 18, in FIG. 3 (continued), reference numeral 320, Line 2, delete "medial" and insert -- medical --.

On sheet 5 of 18, in FIG. 4, reference numeral 400, Line 2, delete "P3TRIAGE" and insert -- PETRIAGE --.

On sheet 6 of 18, in FIG. 5, reference numeral 500, Line 2, delete "P3TRIAGE" and insert -- PETRIAGE --.

On sheet 8 of 18, in FIG. 7, reference numeral 700, Line 2, delete "P3TRIAGE" and insert -- PETRIAGE --.

Signed and Sealed this
Twenty-third Day of May, 2023

Katherine Kelly Vidal
*Director of the United States Patent and Trademark Office*